United States Patent

Persson et al.

[11] Patent Number: 6,046,334
[45] Date of Patent: Apr. 4, 2000

[54] HETEROCYCLIC CHEMICAL COMPOUND

[75] Inventors: Lars Persson, Hassleholm; Nicola Rehnberg, Perstorp, both of Sweden

[73] Assignee: Perstorp AB, Perstorp, Sweden

[21] Appl. No.: 09/068,495

[22] PCT Filed: Oct. 23, 1996

[86] PCT No.: PCT/SE96/01352

§ 371 Date: May 13, 1998

§ 102(e) Date: May 13, 1998

[87] PCT Pub. No.: WO97/18220

PCT Pub. Date: May 22, 1997

[30] Foreign Application Priority Data

Nov. 13, 1995 [SE] Sweden .................................. 9504008

[51] Int. Cl.⁷ .............................. C07F 9/59; C07F 9/572; A61K 31/675

[52] U.S. Cl. ................. 546/25; 548/413; 514/89

[58] Field of Search .................................................. 546/25

[56] References Cited

PUBLICATIONS

Mats Malmberg et al., "A Facile Synthesis of N–Substituted D–Arabino–Piperidinol Phosphates from the Inositol Phosphate α–Trinositol", *Synlett* (Apr. 1996), pp. 361–362.

*Primary Examiner*—Alan L. Rotman
*Attorney, Agent, or Firm*—Scully, Scott, Murphy & Presser

[57] ABSTRACT

The present application is directed to a heterocyclic compound having the structural formula:

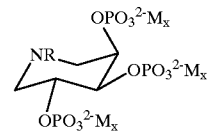

where R is hydrogen, $C_1$–$C_2$ alkyl, cyclohexyl, phenyl, benzyl, phenylethyl, 2-hydroxyethyl, 3-hydroxypropyl, carboxymethyl, 4-(carboxylamine)butyl or diphenylmethyl; M is hydrogen, sodium, potassium, magnesium or ammonium; and x is 1 or 2. The heterocyclic compound having the aforementioned structural formula finds application in many pharmaceutical applications.

7 Claims, No Drawings

HETEROCYCLIC CHEMICAL COMPOUND

CROSS-REFERENCE TO RELATED APPLICATION

This is a national phase application, under 35 U.S.C. §371, of International Application No. PCT/SE96/01352, dated Oct. 23, 1996.

The present invention relates to a heterocyclic chemical compound containing boron, silicon, nitrogen, phosphorous, sulphur, or selenium in the ring structure. In addition the compound is substituted with stereochemically well defined groups. Such compounds are very difficult to bring about.

According to the present invention, it has quite unexpectedly been possible to prepare novel heterocyclic derivatives possessing unexpected physiological properties. The invention relates to a heterocyclic compound of formula 1 or 2

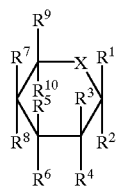

1

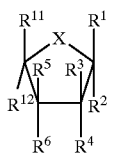

2 or a neutral or acidic salt thereof where the counter ion is $Li^+$, $Na^+$, $K^+$, $Mg^{2+}$, $Ca^{2+}$, $NH_4^+$ or another pharmacologically acceptable positively charged inorganic or organic ion or any combination thereof, where at least one of $R^1$–$R^{12}$ has the formula:

a)

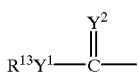

b)

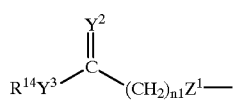

c)

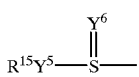

d)

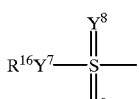

e)

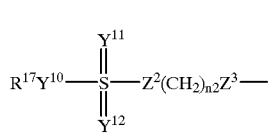

f)

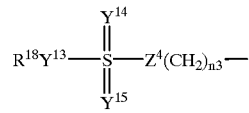

g)

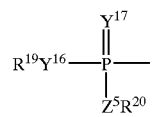

h)

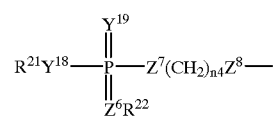

i)

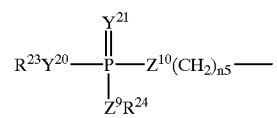

and where the remaining $R^1$–$R^{12}$ can be selected from H, $HY^{22}$, halogen, $R^{25}$, or $R^{26}Y^{23}$;

with the provision that
one of $R^9$ and $R^{10}$ may also be $C(R^{29})_{2-m}(V^1)_m((Y^{24})_pR^{30})$ and
one of $R^{11}$ and $R^{12}$ may also be $C(R^{29})_{2-m}(V^1)_m((Y^{24})_pR^{30})$ or
$C(R^{29})_{1-m}(V^1)_m((Y^{24})_pR^{30})C(R^{31})_{2-q}(V^2)_q((Y^{25})_rR^{32})$;

where
n1, n2, n3, n4, and n5 are 0–4;
$Z^1$ to $Z^{10}$ are $CH_2$, $NR^{27}$, $NOR^{28}$, O, or S;
m, p, q, and r are 0 or 1,
and where
$V^1$ and $V^2$ are a group as defined above in any of the formula a) to i),
and where
X is $BR^{33}$, $Si(R^{33})_2$, $NR^{33}$, $PY^{26}R^{33}$, $PY^{26}Y^{27}R^{33}$, S, SO, $SO_2$, or Se,
$Y^1$ to $Y^{27}$ are $NR^{34}$, $NOR^{35}$, O, or S;
and where
$R^{13}$ to $R^{35}$ are
(1) hydrogen,
(2) a straight or branched saturated or unsaturated alkyl residue containing 1–22 carbon atoms,
(3) a saturated or unsaturated aromatic or non-aromatic homo- or heterocyclic residue containing 3–22 carbon atoms and 0–5 heteroatoms consisting of nitrogen, oxygen, or sulfur,
(4) a straight or branched saturated or unsaturated alkyl residue containing 1–22 carbon atoms substituted with a saturated or unsaturated aromatic or non-aromatic homo- or heterocyclic residue containing 3–22 carbon atoms and 0–5 heteroatoms consisting of nitrogen, oxygen, or sulfur,
(5) a saturated or unsaturated aromatic or non-aromatic homo- or heterocyclic residue containing 3–22 carbon atoms and 0–5 heteroatoms consisting of nitrogen, oxygen, or sulfur, substituted with a straight or branched saturated or unsaturated alkyl residue containing 1–22 carbon atoms,
(6) or a residue of an aminoacid, peptide, or a carbohydrate;

in the said groups 2–6 the residues and/or the substituents thereof being unsubstituted or substituted with 0–6 of the following groups: hydroxy, alkoxy, aryloxy, acyloxy, carboxy, alkoxycarbonyl, alkoxycarbonyloxy, aryloxycarbonyl, karbamoyl, fluoro, chloro, bromo, azido, cyano, oxo, oxa, amino, imino, alkylamino, arylamino, acylamino, nitro, alkylthio, alkylsulfonyl.

Thus, the chemical compound according to the invention may be a derivative of piperidin, tetrahydrothiopyran, S-oxotetrahydrothiopyran, S,S-dioxotetrahydrothiopyran, tetrahydroselenopyran, tetrahydrofuran, pyrrolidine, tetrahydro-thiophene, S-oxotetrahydrothiophene, S,S-dioxotetrahydrothiophene, or tetra-hydroselenophene.

The acidic or negatively charged groups consists of, or derive from, a carboxylic acid, thiocarboxylic acid, carboxamide, sulfonic acid, sulfonamide, phosphate, thiophosphate, phosphonate.

The straight or branched saturated or unsaturated alkyl residue in groups 2–6 above can be exemplified by: methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, doeicosyl, isopropyl, isobutyl, isopentyl, isohexyl, isoheptyl, isooctyl, isononyl, isodecyl, isodoecosyl, 2-butyl, 2-pentyl, 2-hexyl, 2-heptyl, 2-octyl, 2-nonyl, 2-decyl, 2-doeicosyl, 2-methylbutyl, 2-methylpentyl, 2-methylhexyl, 2-methylheptyl, 2-methyloctyl, 2-methylnonyl, 2-methyldecyl, 2-methyleicosyl, 2-ethylbutyl, 2-ethylpentyl, 2-ethylhexyl, 2-ethylheptyl, 2-ethyloctyl, 2-ethylnonyl, 2-ethyldecyl, 2-ethyleicosyl, tertbutyl, ethenyl, propenyl, butenyl, pentenyl, hexenyl, heptenyl, octenyl, nonenyl decenyl, undecenyl, dodecenyl, tridecenyl, tetradecenyl, pentadecenyl, hexadecenyl, heptadecenyl, octadecenyl, nonadecenyl, eicosenyl, heneicosenyl, doeicosenyl, butadienyl, pentadienyl, hexadienyl, heptadienyl, octadienyl, nonadienyl, decadienyl, doeicodienyl, ethynyl, propynyl, doeicosynyl.

The saturated or unsaturated aromatic or non-aromatic homo- or heterocyclic residue in groups 2–6 above can be exemplified by: cyclopropyl, cyclobutyl, cyclopentyl, cyclohexyl, cycloheptyl, cyclooctyl, cyclononyl, cyclodecyl, cycloundecyl, cyclododecyl, cyclotridecyl, cyclotetradecyl, cyclopentadecyl, cyclohexadecyl, cycloheptadecyl, cyclooctadecyl, cyclononadecyl, cycloeicosyl, cycloheneicosyl, cyclodoeicosyl, adamantyl, cyclopropenyl, cyclobutenyl, cyclopentenyl, cyclohexenyl, cycloheptenyl, cyclooctenyl, cyclononenyl, cyclodecenyl, phenyl, biphenyl, naphthyl, hydroxyphenyl, aminophenyl, mercaptophenyl, fluorophenyl, chlorophenyl, azidophenyl, cyanophenyl, carboxyphenyl, alkoxyphenyl, acyloxyphenyl, acylphenyl, oxiranyl, thiiranyl, aziridinyl, oxetanyl, thietanyl, azetidinyl, tetrahydrofuranyl, tetrahydrothiophenyl, pyrrolidinyl tetrahydropyranyl, tetrahydrothiopyranyl, tetrahydrothiophenyl, pyrrolidinyl, tetrahydropyranyl, tetrahydrothiopyranyl, piperidinyl, quinuclidinyl, dioxanyl, dithianyl, trioxanyl, furyl, pyrrolyl, thienyl, pyridyl, quinolyl, benzofuryl, indolyl, benzothienyl, oxazolyl, imidazolyl, thiazolyl, pyridazinyl, pyrimidyl, pyrazinyl, purinyl, or a carbohydrate.

Substituents may be selected from the group of hydroxy, alkoxy, aryloxy, acyloxy, carboxy, alkoxycarbonyl, alkoxycarbonyloxy, aryloxycarbonyl, karbamoyl, fluoro, chloro, bromo, azido, cyano, oxo, oxa, amino, imino, alkylamino, arylamino, acylamino, nitro, alkylthio, and alkylsulfonyl.

A preferred embodiment of the invention is a chemical compound having formula 1 or a neutral or acidic salt thereof where the counter ion is sodium, potassium, magnesium, ammonium, or a another pharmacologically acceptable positively charged inorganic or organic ion or any combination thereof;

X is $NR^{33}$, S, SO, or $SO_2$;

at least one of $R^3$, $R^4$, $R^5$, $R^6$, $R^7$, or $R^8$ is a carboxyl acid, sulfonic acid, phosphoric acid, phosphonic acid, or thiophosphoric acid group;

the remaining of $R^3$, $R^4$, $R^5$, $R^6$, $R^7$, and $R^8$ are hydrogen and $R^1$, $R^2$, $R^9$, and $R^{10}$ are hydrogen and $R^{33}$ is anyone of the members of groups 1–6 above.

Thus the chemical compound according to this embodiment of the invention may be a derivative of piperidin, tetrahydrothiopyran, S-oxotetrahydrothiopyran, S,S-dioxotetrahydrothiopyran.

The acidic or negatively charged groups may be, or derived from, a carboxylic acid, sulfonic acid, phosphate, thiophosphate, or phosphonate.

Preferably X is $NR^{33}$ and at least one of $R^3$, $R^4$, $R^5$, $R^6$, $R^7$, or $R^8$ is $OPO_3H_2$ in a non-geminal arrangement in the above embodiment.

Thus, the chemical compound according to this embodiment of the invention may be a derivative of piperidintriol 3,4,5-trisphosphate.

Another preferred embodiment of the invention is a chemical compound having formula 1 or a neutral or acidic salt thereof where the counter ion is sodium, potassium, or magnesium or any combination thereof;

where X is $NR^{33}$;

three of $R^3$, $R^4$, $R^5$, $R^6$, $R^7$, and $R^8$ are $OPO_3H_2$ in a non-geminal arrangement;

the remaining of $R^3$, $R^4$, $R^5$, $R^6$, $R^7$, and $R^8$ are hydrogen, $R^1$, $R^2$, $R^9$, and $R^{10}$ are hydrogen and $R^{33}$ is anyone of the members of groups 1–6 above.

Thus, the chemical compound according to this embodiment of the invention may be a derivative of 1,5-dideoxy-1,5-iminopentitol 2,3,4-tris(dihydrogen phosphate).

It is specially preferred in this embodiment that $R^3$, $R^5$, and $R^8$ are $OPO_3H_2$ and $R^1$, $R^2$, $R^4$, $R^6$, $R^7$, $R^9$, and $R^{10}$ are hydrogen.

Thus, the chemical compound according to this embodiment of the invention may be a derivative of 1,5-dideoxy-1,5-iminoarabinitol 2,3,4-tris(dihydrogen phosphate) or a neutral or acidic sodium or potassium salt thereof.

Yet another preferred embodiment of the invention relates to a chemical compound having formula 1 or a neutral or acidic salt thereof where the counter ion is sodium, or potassium or any combination thereof where X is $NR^{33}$ and $R^{33}$ is 1) hydrogen;
2) a straight or branched saturated or unsaturated alkyl residue containing 1–16 carbon atoms;
3) a saturated or unsaturated aromatic or non-aromatic homo- or heterocyclic residue containing 1–16 carbon atoms and 0–3 hetreoatoms consisting of nitrogen, oxygen, or sulfur;
4) a straight or branched saturated or unsaturated alkyl residue containing 1–10 carbon atoms substituted with a saturated or unsaturated aromatic or non-aromatic homo- or heterocyclic residue containing 1–10 carbon and 0–3 heteroatoms consisting of nitrogen, oxygen, or sulfur;
5) a saturated or unsaturated aromatic or non-aromatic homo- or heterocyclic residue containing 1–10 carbon atoms and 0–3 heteroatoms consisting of nitrogen, oxygen, or sulfur substituted with a straight or branched saturated or unsaturated alkyl residue containing 1–10 carbon atoms;

6) or a residue of an aminoacid, peptide, or a carbohydrate;

in the said groups 2–6 the residues and/or the substituents thereof being unsubstituted or substituted with 0–6 of the following groups: hydroxy, alkoxy, aryloxy, acyloxy, carboxy, alkoxycarbonyl, alkoxycarbonyloxy, aryloxycarbonyl, karbamoyl, fluoro, chloro, bromo, azido, cyano, oxo, oxa, amino, imino, alkylamino, arylamino, acylamino, nitro, alkylthio, alkylsulfonyl;

$R^3$, $R^5$, and $R^8$ are $OPO_3H_2$ and $R^1$, $R^2$, $R^4$, $R^6$, $R^7$, $R^9$, and $R^{10}$ are hydrogen.

Of particular interest is derivatives where the imino-nitrogen has the formal position of an α-nitrogen of an aminoacid or is a part of an amino-deoxy-carbohydrate.

It is specially preferred in the above embodiment that $R^{33}$ is hydrogen, methyl, dodecyl, benzyl, 2-phenylethyl, 2-(3,4-dimethoxyphenyl)ethyl, 2-hydroxyethyl, 3-hydroxypropyl, carboxymethyl, 3-(dimethylamino)propyl, 2-(4-imidazolyl)ethyl, 4-(benzyloxycarbonylamino)butyl, cyclohexyl, diphenylmethyl, or phenyl.

The present invention also relates to polyphosphorylated or otherwise substituted hexo- and pentofuranosidic compounds exemplified by, but not limited to, methyl α-D-mannofuranoside 2,3,5-trisphosphate and ethyl β-L-arabinofuranoside 2,3,5-trisphosphate.

The present invention also relates to a pharmaceutical composition comprising as a pharmaceutically active ingredient at least one compound defined above. The pharmaceutical composition can consist of a compound of formula 1 or 2 solely or together with an additive, excipient or carrier. It is suitable that the composition exists in unit dosage forms. The administration form could be parenteral such as subcutaneous, intramuscular, or intravenous or non-parenteral such as tablets, granules, or capsules. For administration to human patients appropriate dosages can routinely be determined by those, skilled in the art by extension of results obtained in animals. The preferred dosage for humans falls within the range of 0.1 to 25 mg compound/day/kg body weight. The composition usually contains 0.01–1.5 g, such as 0.05–1.3 g, or preferably, 0.1–1.0 g compound of formula 1 or 2. The compound of formula 1 or 2 may be the only pharmaceutically active ingredient in the composition. However, also other pharmaceutically active ingredients can be present therein. The amount of the compound of formula 1 or 2 should then constitute 5–95% or 15–80% such as 25–60% by weight of said active ingredients.

The invention is further illustrated in connection with the embodiment examples below of which examples 1–15 show production of various compounds within the scope of the invention. Example 16 illustrates the pharmaceutical effect of a compound according to the invention and example 17 shows a toxicological test of a compound according to the invention.

EXAMPLE 1

Reaction formula:

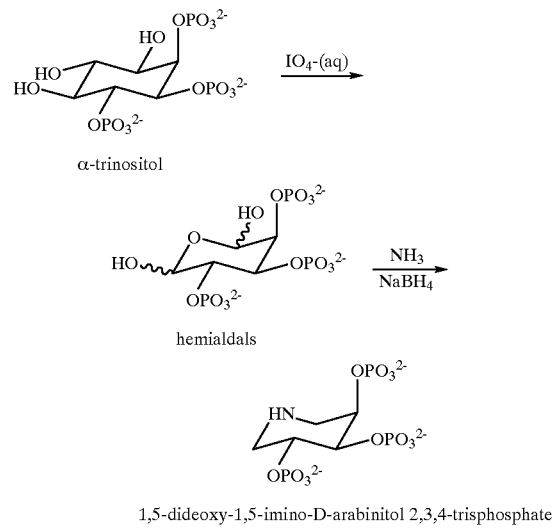

1,5-dideoxy-1,5-imino-D-arabinitol 2,3,4-trisphosphate

α-Trinositol (1D-myo-inositol 1,2,6-trisphosphate sodium salt, 10 g, 18.87 mmol) was dissolved in water (50 ml) and added in one lot to a solution of sodium periodate (4.04 g, 18.87 mmol) and periodic acid (4.3 g, 18.87 mmol) in water (50 ml). Polarimetry indicated complete reaction within 3 hours, but the solution was usually left overnight. If desirable, this solution can be kept refrigerated for at least a week without noticeable deterioration. A closed vessel should be avoided as in a few cases gas was slowly formed.

The oxidation product is a mixture of hemialdals characterized by $^1$H-NMR signals in the region of 5.3–3.2 ppm. To a part of this solution was added ammonia (10 equiv) and sodium borohydride (10 equiv). If the amine was sparingly soluble in the reaction mixture a cosolvent such as ethanol or 1,2-dimethoxyethane was added. The reaction between hemialdals and 3-(dimethylamino)-propylamine was complete within 5 min (polarimetry). The borohydride was added 10 min after the addition of ammonia. The solution was set aside for 1 day.

The solvent was removed by evaporation. Non-volatile hydrophobic amines were removed by partitioning the residue between water and dichloromethane. Removal of solvents gave a residue that was dissolved in a small amount of water and precipitated from a large volume of acetone. The precipitation was repeated once to give a product essentially free of iodide. The precipitate was then dissolved in water and acidified with either acetic acid or an acidic ion exchange resin. Repeated co-evaporation with methanol removed boric acid. Finally, the product was dissolved in water and precipitated from ethanol. Further purification by ion-exchange chromatography gave 1,5-dideoxy-1,5-imino-D-arabinitol 2,3,4-trisphosphate that was characterized as a sodium salt, yield 95%: $[\alpha]_D^{21}$ −4.1° (c 0.8, $H_2O$); $^1$H-NMR ($D_2O$) δ 4.72 (m, 3H, H-2, H-3, H-4), 3.45 (dd, 1H, J=13.4, 2.1 Hz, H-5), 3.38 (dd, 1H, J=12.2, 5.0 Hz, H-2 eq), 3.36 (dd, 1H, J=13.4, 4.8 Hz, H-5), 3.29 (dd, 1H, J=12.2, 9.7 Hz, H-$2_{ax}$), $^{13}$C-NMR ($D_2O$) δ 73.5 (m), 70.6 (dd, J=4.73, 2.48 ppm), 68.5 (t, J=4.30 ppm) 46.3 (s), 45.4 (d, J=4.10 ppm), $^{31}$P-NMR ($D_2O$) 67 3.15, 2.73, 2.04; IR spectra confirmed the structure of the compound.

EXAMPLE 2

The method disclosed in example 1 gave, when ammonia was replaced by 2-phenylethylamine, 1,5-dideoxy-1,5- imino-N-(2-phenylethyl)-D-arabinitol 2,3,4-trisphosphate. It was purified by ion-exchange chromatography and characterized as sodium salt, yield 85%: $[\alpha]_D^{21}$ −10.6° (c, 0.3, $H_2O$), $^1$H-NMR ($D_2O$) δ 7.48–7.3 (m, 5H, ArH), 4.78–4.52 (m, 3H, H-2, H-3, H-4), 3.8–3.2 (m, 4H, H-2, H-5), 3.55–3.40 (m, 2H, $CH_2$), 3.15 (t, 2H, J=8.6 Hz, $CH_2$), at 8020 C. the multiplett of H-2, H-3, H-4 separates into three signals but still with a complicated coupling pattern; $^{13}$C-NMR ($D_2O$) δ 139.3, 131.8, 131.7, 130.0 (ArC), 72.0, 71.0, 68.3 (C-2, C-3, C-4), 60.8 ($NCH_2$), 54.2, 52.4 ($CH_2CHO$), 32.5 ($CH_2$), $^{31}$P-NMR ($D_2O$) δ 3.19, 2.79, 2.10; IR spectra confirmed the structure of the compound.

EXAMPLE 3

The method disclosed in example 1 gave, when ammonia was replaced by methylamine, 1,5-dideoxy-1,5-imino-N-methyl-D-arabinitol 2,3,4-trisphosphate. It was characterized as a sodium salt, yield 91%.

EXAMPLE 4

The method disclosed in example 1 gave, when ammonia was replaced by dodecylamine, synthesis of 1,5-dideoxy-N-dodecyl-1,5-imino-D-arabinitol 2,3,4-trisphosphate. It was characterized as a sodium salt, yield 80%.

EXAMPLE 5

The method disclosed in example 1 gave, when ammonia was replaced by benzylamine, N-benzyl-1,5-dideoxy-1,5-imino-D-arabinitol 2,3,4-trisphosphate. It was characterized as a sodium salt, yield 89%.

EXAMPLE 6

The method disclosed in example 1 gave, when ammonia was replaced by 2-(3,4-dimethoxyphenyl)ethylamine, 1,5-dideoxy-N-[2-(3,4-dimethoxyphenyl)ethyl]-1,5-imino-D-arabinitol 2,3,4-trisphosphate. It was characterized as a sodium salt, 88%.

EXAMPLE 7

The method disclosed in example 1 gave, when ammonia was replaced by 2-hydroxyetylamine, 1,5-dideoxy-N-(2-hydroxyethyl)-1,5-imino-D-arabinitol 2,3,4-trisphosphate. It was characterized as a sodium salt, yield 93%.

EXAMPLE 8

The method disclosed in example 1 gave, when ammonia was replaced by 3-hydroxypropylamine, 1,5-dideoxy-N-(3-hydroxypropyl)-1,5-imino-D-arabinitol 2,3,4-trisphosphate. It was characterized as a sodium salt, yield 91%.

EXAMPLE 9

The method disclosed in example 1 gave, when ammonia was replaced by glycine, N-carboxymethyl-1,5-dideoxy-1,5-imino-D-arabinitol 2,3,4-trisphosphate. It was characterized as a sodium salt, yield 82%.

EXAMPLE 10

The method disclosed in example 1 gave, when ammonia was replaced by 3-(dimethylamino)propylamine, 1,5-dideoxy-N-[2-dimetylamino)propyl]-1,5-imino-D-arabinitol 2,3,4-trisphosphate. It was characterized as a sodium salt, yield 90%.

EXAMPLE 11

The method disclosed in example 1 gave, when ammonia was replaced by 2-(4-imidazolyl)etylamine, 1,5-dideoxy-N-[2-(4-imidazoly)ethyl]-1,5-imino-D-arabinitol 2,3,4-trisphosphate. It was characterized as a sodium salt, yield 85%.

EXAMPLE 12

The method disclosed in example 1 gave, when ammonia was replaced by 4-(benzyloxycarbonylamino)butylamine, N-[4-(benzyloxycarbonylamino)butyl]-1,5-dideoxy-1,5-imino-D-arabinitol 2,3,4-trisphosphate. It was characterized as a sodium salt, yield 81%.

EXAMPLE 13

The method disclosed in example 1 gave, when ammonia was replaced by cyclohexylamine, N-cyclohexyl-1,5-dideoxy-1,5-imino-D-arabinitol 2,3,4-trisphosphate. It was characterized as a sodium salt, yield 87%.

EXAMPLE 14

The method disclosed in example 1 gave, when ammonia was replaced by diphenylmethylamine, 1,5-dideoxy-N-diphenylmetyl-1,5-imino-D-arabinitol 2,3,4-trisphosphate. It was characterized as a sodium salt, yield 83%.

EXAMPLE 15

The method disclosed in example 1 gave, when ammonia was replaced by aniline, 1,5-dideoxy-1,5-imino-N-phenyl-D-arabinitol 2,3,4-trisphosphate. It was characterized as a sodium salt, yield 70%: $^1$H-NMR ($D_2O$) δ 7.38 (t, 2H, J=7.7 Hz, m-ArH), 7.20 (d, 2H, J=8.0 Hz, o-ArH), 7.07 (t, 1H, J=7.1 Hz, p-ArH), 4.68 (tq, 1H, J=6.6, 3.2 Hz, POCH), 4.52 (dtd, 1H, J=9.0, 7.0, 3.6 Hz, POCH), 4.36 (td, 1H, J=8.4, 3.2 Hz, POCH), 3.61 (dd, 1H, J=13.0, 1.0 Hz, NCH), 3.55 (dd, 1H, J=13.0, 6.5 Hz, NCH), 3.24 (dd, 1H, J=12.4, 2.9 Hz, NCH), 3.17 (dd, 13.0, 6.5 Hz, NCH); $^{13}$C-NMR ($D_2O$) δ 153.4, 132.3, 124.3, 120.9, 76.8 (m), 73.6 (t, J=5.1 Hz), 73.0, 54.8, 54.5; $^{31}$P-NMR 1.8, 1.7, 1.6.

The products in example 3 to 14 gave $^1$H-NMR spectra of poor resolution with ring $^1$H-signals at approximately 4.8–4.5 and 3.6–2.9 ppm, $^{13}$C-signals at 78–65 and 56–44 ppm, and $^{31}$P-signals at 5–3 ppm.

EXAMPLE 16

This method follows that described by Winter et al (C. A. Winter, G. A. Risley, and G. W Nuss, *Proc. Soc. Exp. Biol. Med.*, 1962, 111, 544) and is used to evaluate the antiinflammatory effects of drugs.

Mice were injected with carrageenan solution into the lower surface of both hind-paws (0.75 mg per paw, in 0.05 ml); an increase in paw weight indicates inflammation (edema). 3.5 hours later, the animals were sacrificed by a blow to the cervical vertebrae and the hind-paws sectioned and weighted.

10 mice were studied per group. The test was performed blind.

N-(2-phenylethyl)-1,5-dideoxy-1,5-imino-D-arabinitol 2,3,4-trisphosphate sodium salt was examined at the dose of 64 mg/kg, administered i.v., 5 minutes before carrageenan (i.e. 3 h 35 min before paw section).

Results: N-(2-phenylethyl)-1,5-dideoxy-1,5-imino-D-arabinitol 2,3,4-trisphosphate sodium salt significantly reduced the elevated hind-paw weight induced by intraplantar injection of carrageenan; paw weight was decreased by 27% after this treatment.

EXAMPLE 17

The method follows that described by Irwin (S. Irwin, *Psychopharmacologica*, 1968, 13, 222) and is used to detect general physiological, behavorial and toxic effects of drugs, and indicates the range of doses that can be used for later experiments.

Mice (3 per dose) were administered N-(2-phenylethyl)-1,5-dideoxy-1,5-imino-D-arabinitol 2,3,4-trisphosphate sodium salt and were observed in comparison with a control group given vehicle.

Behavorial modification, neurotoxicity symptoms, pupil diameter and rectal temperature were recorded according to a standardized observation grid adapted from that described by Irwin. The grid contains the following items: mortality, sedation, excitation, aggressiveness, straub, writhes, convulsions, tremor, exophthalamos, salivation, lacrimation, piloerection, defecation, fear, traction, reactivity to touch, loss of righting reflex, sleep, motor incoordination, muscle tone, stereotypies, catalepsy, grasping, ptosis, difficulty in respiration, corneal reflex, analgesia, gait, rectal temperature, and pupil diameter.

Observations were performed 15, 30, 60, 120, and 180 minutes after administration of the test substance and also 24 h later.

N-(2-phenylethyl)-1,5-dideoxy-1,5-imino-D-arabinitol 2,3,4-trisphosphate sodium salt was examined at the following doses: 128, 256, and 512 mg/kg administered i.v.

Result: Straub was seen for one of three mice after 15 minutes at the dose of 512 mg/kg, no other reaction was observed.

We claim:
1. A heterocyclic compound having the structural formula

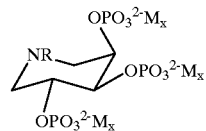

where R is hydrogen, $C_1$–$C_2$ alkyl, cyclohexyl, phenyl, benzyl, phenylethyl, 2-hydroxyethyl, 3-hydroxypropyl, carboxymethyl, 4-(carboxylamine)butyl or diphenylmethyl; M is hydrogen, sodium, potassium, magnesium or ammonium; and x is 1 or 2.

2. A compound in accordance with claim 1 wherein M is hydrogen; and x is 2.

3. A compound in accordance with claim 1 where M is sodium; and x is 2.

4. A compound in accordance with claim 1 where M is potassium; and x is 2.

5. A compound in accordance with claim 1 wherein M is magnesium; and x is 1.

6. A compound in accordance with claim 1 wherein M is ammonium; and x is 2.

7. A compound in accordance with claim 1 wherein R is hydrogen.

* * * * *